United States Patent [19]
Mitchell

[11] 3,940,952
[45] Mar. 2, 1976

[54] DETECTING ABNORMALITY

[75] Inventor: Drury K. Mitchell, Columbus, Ohio

[73] Assignee: Battelle Memorial Institute, Columbus, Ohio

[22] Filed: Oct. 23, 1973

[21] Appl. No.: 408,292

[52] U.S. Cl. .......................... 73/67.8 R; 73/71.5 US
[51] Int. Cl.² ...................................... G01N 29/04
[58] Field of Search ............ 73/67.7, 67.8 R, 67.8 S, 73/67.9, 71.5 US, 67.2; 310/8, 8.2, 8.3, 8.7

[56]  References Cited
UNITED STATES PATENTS

| | | | |
|---|---|---|---|
| 3,280,621 | 10/1966 | Cardinal et al. | 73/67.8 S |
| 3,470,868 | 10/1969 | Krause et al. | 73/67.8 S |
| 3,482,434 | 12/1969 | Cowan et al. | 73/67.8 R |
| 3,518,697 | 6/1970 | Martens | 73/67.8 S X |
| 3,606,791 | 9/1971 | Rathburn et al. | 73/71.5 US |
| 3,721,312 | 3/1973 | St. John | 73/67.7 |
| 3,817,089 | 6/1974 | Eggleton | 73/67.8 S |

Primary Examiner—Richard C. Queisser
Assistant Examiner—Stephen A. Kreitman
Attorney, Agent, or Firm—Philip M. Dunson

[57] ABSTRACT

Apparatus for detecting an abnormality such as a discontinuity in a predetermined region of a material by directing an elastic mechanical wave, such as an ultrasonic or other acoustic wave, in a series of pulses to portions of the region and providing response to the wave pulses reflected therefrom. The amplitudes of pulses reflected from a normal portion of the region may approximate the amplitudes of pulses reflected from a portion where an abnormality is present and thus make it difficult to distinguish between such portions.

The directed wave is varied, as by rotating a transducer having an irregular cross-sectional radiation pattern, to provide randomlike variations in the shapes of successive pulses where reflected from a normal portion, differing detectably from any variations caused in the pulses where reflected from an abnormal portion.

Means responsive to a plurality of successive reflected pulses are provided for effectively superimposing them, either electrically or in an overlaid visual display, the types of wave shapes of the superimposed pulses being indicative selectively of a normal or an abnormal portion of the region.

11 Claims, 4 Drawing Figures

DETECTING ABNORMALITY

BACKGROUND

Existing ultrasonic pulse-echo techniques rely principally on a comparison of the amplitudes of the signal and noise responses, commonly called the signal to noise ratio, for the proper identification of a flaw. Reliability of defect detection, therefore, requires this signal-to-noise ratio to be substantially greater than unity. The present invention provides additional distinguishing characteristics of flaw and noise responses, namely, motion, which permits defect identification under conditions of unfavorable signal-to-noise ratios. In a typical embodiment the transducer is continuously rotated about its longitudinal axis as it scans the surface of the material being inspected. The result is a dynamic display on the face of the cathode ray tube of the pulser/receiver where the apparent motion of the noise responses differ from that of a flaw.

One of the most vexing limitations to the ultrasonic pulse-echo inspection method is imposed by spurious signals that accompany the response from a true material flaw. In order to identify a flaw against this background, it is necessary that the amplitude of the flaw signal be substantially greater than those of the spurious signals, commonly called noise. That is, the signal-to-noise ratio must be favorable by exceeding unity an amount dependent on the skill and experience of the particular operator. A highly skilled operator may sometimes be able to use other characteristics than amplitude for flaw identification. The flaw of interest may have a particular shaped response or the duration of its response, as the surface is scanned, may be longer than the accompanying noise responses. These situations, however, are too rare and subjective to be considered a practical solution to the unfavorable signal-to-noise ratio problem.

Noise may be considered to be of two types which for our purpose can be called electronic and acoustic. Electronic noise can originate internally from the inspection equipment or from some external radiating source. It is characterized by being random or time independent and by having a high frequency content. Improved circuitry design, instrument construction, proper shielding, the use of solid-state components, and selective filtering have virtually eliminated electronic noise as a problem. Only under inspection conditions requiring very high gain, when it appears as "grass" along the base line, does it become a factor of any significance. Signal processing involving signal averaging and selective filtering can be used to improve the reliability in the above case.

Acoustic noise, however, has the same characteristics as the response from an actual flaw. Because it is composed of true reflections, it is time dependent and has the same frequency content as the flaw response. Time dependence means that if the transducer remains stationary, the displayed noise responses will not change position, shape or amplitude. They are also repeatable each time the transducer is returned to the same location. Because of the above characteristics, the techniques used to reduce electronic noise are not applicable. (Rothman, Eugene, "Electronic Signal Processing Techniques", Phase I and II, ARPA Order No. 1246, Contract No. DAAA25-69-C-0206 (July, 1969, and May, 1970).)

Each noise response is composed of numerous reflections from small discontinuities randomly scattered throughtout and/or on the surface of the material under inspection. These reflections return by different paths and those arriving the same time at the transducer are summed by the instrument and displayed as a single response. Each noise response therefore is the result of a particular group of small reflectors. These reflectors are caused by material features such as grain boundaries, precipitates, surface roughness, or any other points of abrupt change in acoustic impedance. Although the characteristics of the noise and flaw responses are the same, there is a difference in the nature of their source. Whereas the noise response is from a group of randomly scattered reflectors, the source of the flaw response, practically speaking, is a definite intercepted area and a fixed location in the part.

Investigations have been conducted by others where signal processing methods were used to increase an unfavorable signal-to-noise ratio to a value where the flaw response can be identified. One method consisted of adding the amplitudes of the response signals coming from a plane a fixed distance below the top surface of the material, for a discrete time interval, as the transducer moved along at a constant linear speed. Since during this time interval as the amplitude of a flaw response was more stable than any noise response, the resulting summation of the flaw response was substantially greater than any noise response. In effect, the signal-to-noise ratio was increased. (Ermolov, I. N. and Pilin, B. P., Possible Ways of Improving the Sensitivity of Ultrasonic Inspection of Parts with a Large-Grain Structure, Soviet Journal of Nondestructive Testing (Jan-Feb, 1969) Vol 1, pp46–49.)

Another method consisted of linearly scanning a plane a fixed distance below the surface of the material with an array of transducers positioned at different incident angles. The responses of the transducers were multiplied by each other. Since the amplitude of the flaw responses were more stable than any noise responses, the product of the former was substantially greater than the latter. Again, the result was an increase in the signal-to-noise ratio. (Kennedy, J. C. and Woodmansee, W. E., "Electronic Signal Processing Techniques," Phase III, ARPA Order No. 1246, Contract DAAA 25-69-C-0206 (Jan, 1972).)

A current investigation is being conducted with the objective of enhancing the flaw response by signal averaging a number of wave form responses as the transducer oscillates horizontally while scanning the material. (Regalbuto. J. A., "Nondestructive Testing of Diffusion-Bonded Titanium Alloys for Engine and Airframe Components," First Semiannual Interim Technical Report, Air Force Materials Laboratory Contract F33615-72-C-1705 Project 7351 (June, 1972).)

SUMMARY OF THE INVENTION

Typical apparatus according to the present invention for detecting a selected type of abnormality in a predetermined region by directing an elastic mechanical wave in a series of pulses to portions of the region and providing response to the wave pulses reflected therefrom, wherein the amplitudes of pulses reflected from a portion of the region where such type of abnormality is absent (a normal portion) may approximate the amplitudes of pulses reflected from a portion where such type of abnormality is present (an abnormal portion) and thus make it difficult to distinguish between normal and abnormal portions, includes the improvement comprising means for varying the directed wave in such manner as to provide randomlike variations in the shapes of successive pulses where reflected from a normal portion of the region differing detectably from any such variations caused in successive pulses where reflected from an abnormal portion, and means responsive to a plurality of successive reflected pulses for effectively superimposing them, the types of wave shapes of the superimposed pulses being indicative selectively of a normal or an abnormal portion of the region. The type of abnormality to be detected typically comprises a discontinuity in a material, and the mechanical wave typically is an acoustic wave, such as an ultrasonic wave. The response to the reflected wave pulses typically includes converting them to electrical pulses.

Typically the mechanical wave is generated by means having an irregular cross-sectional radiation pattern and the varying means includes means for providing rapid relative lateral motion between the wave-generating means and the predetermined region, as by continuously rotating the wave-generating means. Typical wave-generating means comprises a transducer that converts a first electrical pulse to a mechanical pulse, then receives the reflected mechanical pulse and converts it to an electrical pulse, then converts a second electrical pulse, and so on, alternately transmitting and receiving, whereby the motion-providing means varies not only the directed wave but also the receiving conversion characteristics and thus provides randomlike variations also in the reception of the reflected pulses.

In some typical embodiments of the invention the superimposing means comprises means for providing an overlaid visual display of the shapes of the successive reflected pulses. Such a display typically is provided as a graph of amplitude as a function of depth in a portion of the region, and the randomlike variations cause apparent motion in the graph that is discriminably different for normal and abnormal portions of the region. Typically the apparent motion for a normal portion of the region is substantial and erratic in both the amplitude direction and the depth direction, and the apparent motion for an abnormal portion is substantial but cyclic in the amplitude direction, providing the maximum obtainable amplitude, and is insubstantial in the depth direction.

In other typical embodiments of the invention the superimposing means comprises means for combining the converted successive reflected pulses electrically, and means responsive to the electrically combined pulses for indicating the location of an abnormal portion of the region. The indicating means typically comprises analog to digital conversion means and digital data processing means responsive thereto. The randomlike variations typically cause substantial and erratic variations in both the amplitude and the time of the peaks of the combined pulses for a normal portion of the region, and cause substantial but cyclic variations in the amplitude, providing the maximum obtainable amplitude, and only insubstantial variations in the time of the peaks of the combined pulses for an abnormal region; and means responsive to the amplitude and the time of the peaks of the combined pulses may be provided for indicating the location of an abnormal portion of the region.

DESCRIPTION OF PREFERRED EMBODIMENTS

Figure 1:
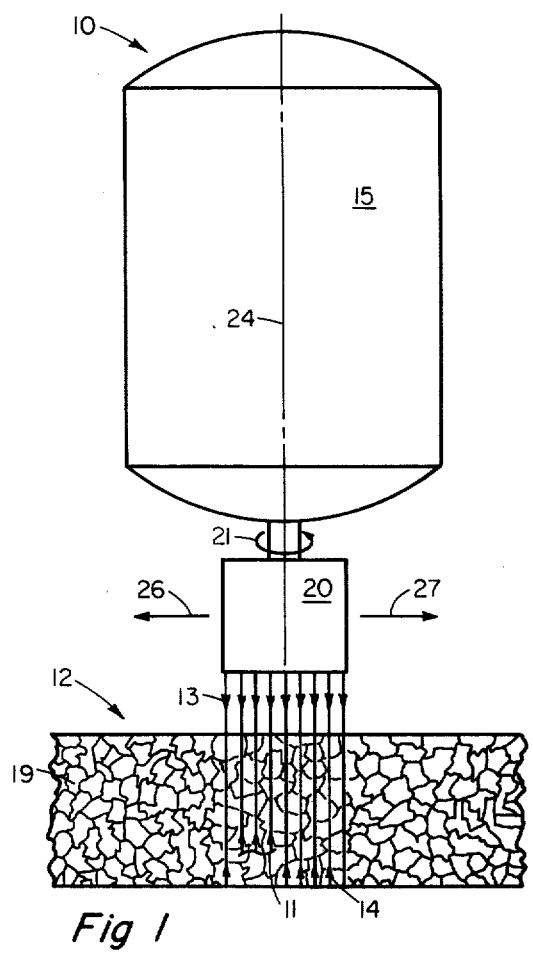
FIG. 1 is a schematic front view illustrating typical embodiments of the present invention.
Figure 2:
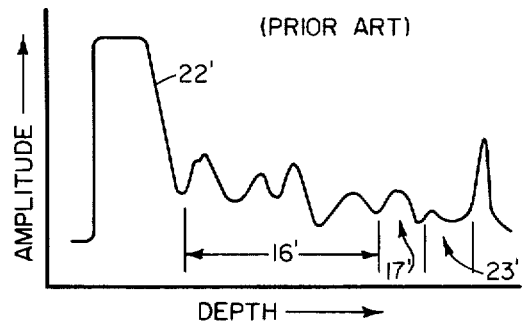
FIG. 2 is a diagrammatic presentation of a typical display obtained with abnormality detecting apparatus of the prior art for a portion of a region as in FIG. 1.

FIG. 1 schematically illustrates typical apparatus 10 according to the present invention for detecting a selected type of abnormality 11 in a predetermined region 12 by directing an elastic mechanical wave 13 in a series of pulses to portions of the region 12 and providing response to the wave pulses reflected therefrom (as indicated typically at 14), wherein the amplitudes of pulses 16' reflected from a portion of the region where such type of abnormality is absent (a normal portion of the region 12) may approximate the amplitudes of pulses 17' reflected from a portion where such type of abnormality is present (an abnormal portion 11) and thus make it difficult to distinguish between normal and abnormal portions, as illustrated in FIG. 2.

Figure 3:
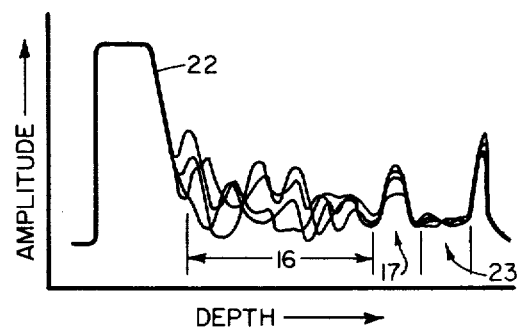
FIG. 3 is a diagrammatic presentation of a typical display obtained with abnormality detecting apparatus according to the present invention for the same portion as in the display of FIG. 2.
Figure 4:
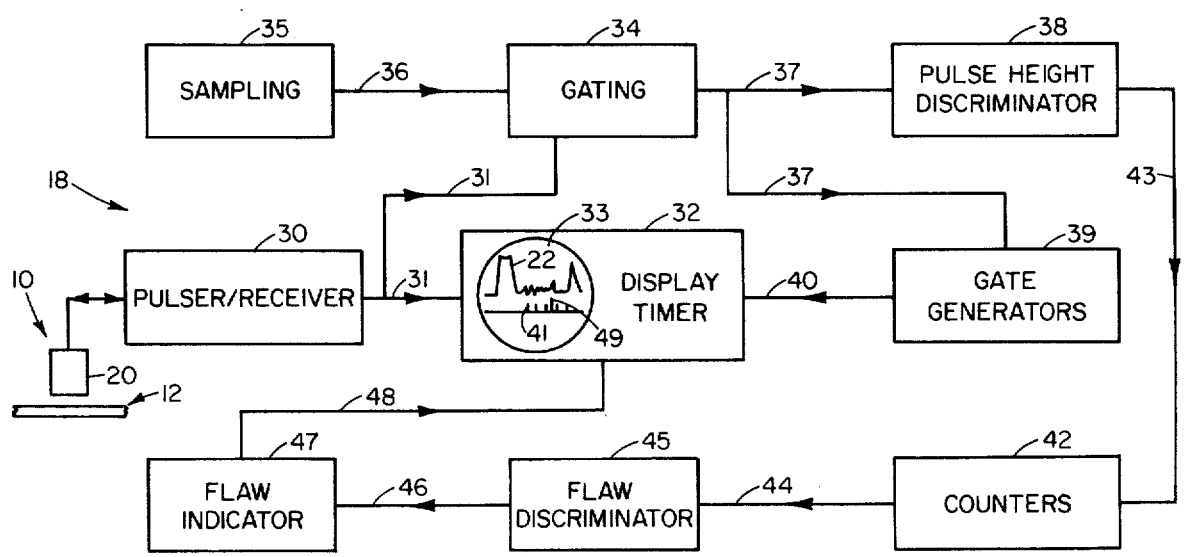
FIG. 4 is a block diagram of typical signal processing apparatus that may be used in the present invention.

An important feature of the apparatus 10 is the improvement comprising means 15 for varying the directed wave 13 in such manner as to provide randomlike variations in the shapes of successive pulses where reflected from a normal portion of the region, as at 16 in FIG. 3, differing detectably from any such variations caused in successive pulses where reflected from an abnormal portion 11, as at 17 in FIG. 3, and means 18, as in FIG. 4, responsive to a plurality of successive reflected pulses for effectively superimposing them, as in FIG. 3, the types of wave shapes of the superimposed pulses being indicative selectively of a normal or an abnormal portion of the region 12.

The type of abnormality to be detected typically comprises a discontinuity 11 in a material 19, and the mechanical wave 13 typically is an acoustic wave, such as an ultrasonic wave. The response to the reflected wave pulses 14 typically includes converting them to electrical pulses.

Typically the mechanical wave 13 is generated by means such as a transducer 20 having an irregular cross-sectional radiation pattern and the varying mean includes means (such as a motor 15, as diagrammatically illustrated in FIG. 1) for providing rapid relative lateral motion between the wave-generating means 20 and the predetermined region 12, as by continuously rotating the wave-generating means 20, as indicated at 21.

The wave generating means typically comprises a transducer 20 that converts a first electrical pulse to a mechanical pulse 13, then receives the reflected mechanical pulse 14 and converts it to an electrical pulse, then converts a second electrical pulse 13, and so on, alternately transmitting and receiving, whereby the motion-providing means (at 21) varies not only the directed wave 13 but also the receiving conversion characteristics and thus provides randomlike variations also in the reception of the reflected pulses 14.

Where the superimposing means 18 comprises means for providing an overlaid visual display of the shapes of the successive reflected pulses, as illustrated in FIG. 3, the display typically is provided as a graph 22 of amplitude as a function of depth in a portion of the region 12, and the randomlike variations cause apparent motion in the graph, as at 16, 17, and 23, that is discriminably different for normal and abnormal portions of the region. Typically the apparent motion for a normal portion of the region 12 is substantial and erratic in both the amplitude direction (vertical) and the depth direction (horizontal), as at 16 and 23; and the apparent motion for an abnormal portion is substantial but cyclic in the amplitude direction (vertical), providing the maximum obtainable amplitude, and is substantial in the depth direction (horizontal), as at 17.

Where the superimposing means 18 comprises means for combining the converted successive reflected pulses electrically, and means responsive to the electrically combined pulses for indicating the location of an abnormal portion 11 of the region 12, the indicating means typically comprises analog to digital conversion means and digital data processing means responsive thereto. Such means are well known and the choice of suitable conversion and processing means for use in specific embodiments of the invention is within the skill of the art. The randomlike variations typically cause substantial and erratic variations in both the amplitude and the time of the peaks of the combined pulses for a normal portion of the region, and cause substantial but cyclic variations in the amplitude, providing the maximum obtainable amplitude, and only insubstantial variations in the time of the peaks of the combined pulses for an abnormal region. This is apparent from FIG. 3, depth being proportional to time. Thus appropriate means responsive to the amplitude and the time of the peaks of the combined pulses may be provided for indicating the location of an abnormal portion 11 of the region 12.

FIG. 4 illustrates the principal functions and operation of a typical signal processing system 18. The pulser/receiver 30 activates the transducer 20 in the normal manner for pulse-echo inspection. The response signal 31 is fed into the display/timer 32 where it is displayed as a video trace 22 on the face of the cathode ray tube (CRT) 33. The response signal 31 also goes to the gating circuits 34.

The sampling circuit 35 generates a continuous series of equally spaced pulses 36 each one of which is fed to the gating circuits 34. The receipt of a pulse from the sampling circuit 35 activates a circuit in the gating circuit group which sets that group in the operating mode. Since there are a definite number of pulses per revolution of the transducer, each pulse occurs when the transducer is at a definite angular position within any one revolution. By adjusting the interval between pulses the number of these positions per revolution can be increased or decreased.

The gating circuit 34 processes the first response signal 31 that arrives from the pulser/receiver 30 after the pulse 36 from the sampling circuit. Only one response signal per transducer position is processed. The operation of the gating circuits consists of opening and then closing each one of a series of a number of gates, in sequence. The time from the opening of the first to the closing of the last determines the range within the material to be inspected. Each gate is open for the same length of time, and by adjusting this time, the inspection range can be increased or decreased. Thus, that part of the signal corresponding to the responses from the inspection range is divided into discrete time intervals. The start of gate operation is delayed for a preset time after the arrival of the top surface response of the sample signal to be processed. By adjusting the preset time, the location of the inspection range within the part can be varied. The closing of the last gate resets the gate activating circuit and counter to be ready to process the succeeding sample signal.

The portion of the sample signal 37 that occurs during the open time of each gate is fed to the pulse height discriminating circuit 38. An amplitude level is preset in that circuit so that only those portions of the signal within each gate that exceed that level are counted.

The gating circuits 34 also activate the gate generators 39 which feed into the display timer 32 a series of pulses 40 the interval between which correspond to the time that the gates are open. These pulses 40 appear as equally spaced pips 41 on the marker trace of the CRT 33. They visually represent the location of the inspection range within the material and the portion within the range that each discrete time interval covers.

There is one counter 42 for each gate. Each time the portion of the signal 37 within a particular gate exceeds the predetermined amplitude during one revolution of the transducer 20 a pulse 43 is transmitted to the counter 42 for that particular gate. Each counter 42 sums the number of times the portion of the signal 37 within its gate exceeds the predetermined amplitude level during one revolution of the transducer 20. At the completion of each revolution the sum of the counts in each gate is fed, as indicated at 44, to the flaw discriminator 45.

Preset in the flaw discriminator 45 is a count level that must be exceeded by the count from any gate in order to be classified as a flaw at the location in the inspection range covered by the particular gate.

When such a condition occurs, the flaw discriminator 45 transmits a pulse 46 to the flaw indicator 47, which generates a pulse 48, to the display/timer 32. This pulse 48 appears as a taller pip 49 on the marker trace of the CRT 33 within the space representing the inspection range location of that particular gate.

In a typical embodiment as in FIG. 1, the apparatus 10 automatically provides apparent motion to the noise and flaw responses of an A-scan display as in FIG. 3 by continuously rotating the transducer 20. Characteristic differences between the apparent motion of the two responses permit the operator to identify a flaw response even though its amplitude may not exceed the noise level.

The inspection procedure may be the same as in the standard pulse-echo method, except that the transducer 20 is continuously rotating. The effect of the rotation is to change the A-scan display from one that is static, as in FIG. 2, or at best slowly changing while linearly scanning, to one that is highly dynamic as in FIG. 3. This dynamic display is caused by the apparent motion of the noise and flaw responses. The apparent motion is due to the fact that successive traces, corresponding to different angular positions of the transducer 20, are not identical and when superimposed give the same effect as that of a motion picture.

There are four characteristics of the dynamic display as in FIG. 3 which singularly or in various combinations assist the operator in distinguishing a flaw response from the accompanying noise. (1) The amplitude of the flaw response 17 is the maximum obtainable for the particular inspection conditions at one or more times during each revolution. (2) The flaw response 17 remains at a fixed horizontal location while the noise responses 16, 23 move back and forth horizontally. (3) The amplitude of the flaw response 17 rises and falls in a smooth cyclic manner while the noise responses 16, 23 do so more erratically. (4) The basic shape of the flaw response 17 changes less than do those of the noise responses 16, 23. For the purpose of clarity, the display in FIG. 3 shows only four successive pulses 13. Ordinarily many more are displayed and the contrast between the responses at 17 an at 16, 23 is still greater than it is in FIG. 3.

A liquid-filled chamber (not shown) may be provided around the transducer 20 for contact testing. The lower end of the chamber may be fitted with a flexible membrane cover to serve as the acoustic window through which the ultrasound may enter the material 19. For longitudinal wave inspection, the window should be perpendicular to the axis 24 of the apparatus 10. For shear wave inspection, it may be at any desired angle to the axis 24.

To detect flaws over the entire region 12, the apparatus 10 may be moved laterally, as indicated at 26 and 27, to scan the region 12 in any convenient manner. The scanning movements 26, 27 typically are much slower than the speed of rotation 21, and are not related to the improvements achieved with the present invention. The apparatus 10 operates in the same way whether positioned over a particular portion (as 16, 17, or 23) or scanning (26, 27) over the region 12.

With the perfect transducer, intensity and travel direction are symmetrical about the central axis. Thus, rotating the transducer about its longitudinal axis, the effect on both the noise or the defect responses would be the same. Practically speaking, asymetry will be present in all transducers. This is the result of imperfections in the transducer itself caused by unavoidable things such as: (1) Inhomogeneity of the piezoelectric, damping, facing, conductive coating, and bonding materials. (2) Dimensional variations in piezoelectric, damping, and facing components. (3) Variations in surface conditions of and thickness of bond lines between components. (4) Variations in the housing geometry and the mounting of transducer components. The same effects due to transducer imperfections may be obtained by such artificial means as offsetting the transducer from the axis of rotation, roughening the face of the transducer, polishing the transducer at a slight angle to the axis of rotation, and attaching a flat wedge-shaped lens to the face of the transducer.

The asymetry due in whole or in part to differences in direction of beam travel at the various cross-sectional locations in the field, results in the noise responses originating from different groups of small randomly scattered reflectors as the transducer assumes various angular positions. Simply expressed, the transducer "looks" at the material structure in different ways as it rotates through one revolution. This causes the arrival time of the noise reflections at the transducer to vary so there is a horizontal shift in the noise responses from one angular position to another. However, since the flaw response is the reflection from a fixed location in the material, it remains time dependent throughout the revolution.

The asymetry due to both localized differences in intensity and/or direction in beam travel causes the amplitudes of both the noise and flaw responses to vary. The area of the flaw being substantially constant, the amplitude of its response is chiefly affected by the characteristics of the cross-sectional pattern of the beam and appears to rise and fall in a smooth cyclic motion as the areas of different intensity and/or beam travel sweep across it. The amplitude of the noise signals also appears to rise and fall, but at a different rate and with a distinctly less rhythmical motion.

Tests show that the present invention is useful for inspecting under conditions where flaws cannot be distinguished from background noise by amplitude only. In a test conducted on CF8 cast stainless steel standard, for example, the response from a 1/32-inch-diameter flat-bottom hole was identified, although its amplitude did not exceed the accompanying noise level.

While the forms of the invention herein disclosed consititute presently preferred embodiments, many others are possible. It is not intended herein to mention all of the possible equivalent forms or ramifications of the invention. It is to be understood that the terms used herein are merely descriptive rather than limiting, and that various changes may be made without departing from the spirit or scope of the invention.

I claim:

1. In apparatus for detecting a selected type of abnormality in a predetermined region comprising transmitter means for directing an elastic mechanical wave in a series of pulses to portions of the region and receiver means for providing response to the wave pulses reflected therefrom, wherein the amplitudes of pulses reflected from a portion of the region where such type of abnormality is absent (a normal portion) may approximate the amplitudes of pulses reflected from a portion where such type of abnormality is present (an abnormal portion) and thus make it difficult to distinguish between normal and abnormal portions, the improvement comprising in the transmitter means, mechanical wave radiating means providing an irregular cross-sectional radiation pattern, means for providing relative transverse repetitive motion between the radiating means and a given portion of the region while a series of pulses are directed to the same portion of the region, superimposed on any scanning movement from portion to portion of the region, to provide randomlike variations in the shapes of successive pulses where reflected from a normal portion of the region differing detectably from any variations caused in successive pulses where reflected from an abnormal portion, and means responsive to a plurality of successive reflected pulses for effectively superimposing them, the types of wave shapes of the superimposed pulses being indicative selectively of a normal or an abnormal portion of the region.

2. Apparatus as in claim 1, wherein the radiating means comprises means for radiating an acoustic wave to the region.

3. Apparatus as in claim 1, wherein the receiver means includes means for converting the reflected wave pulses to electrical pulses.

4. Apparatus as in claim 1, wherein the motion-providing means comprises means for rotating the radiating means.

5. Apparatus as in claim 1, wherein the radiating means comprises a transducer that converts a first electrical pulse to a mechanical pulse, then receives the reflected mechanical pulse and converts it to an electrical pulse, then converts a second electrical pulse, and so on, alternatively transmitting and receiving, whereby the motion-providing means varies not only the directed wave but also the receiving conversion characteristics and thus provides randomlike variations also in the reception of the reflected pulses.

6. Apparatus as in claim 1, wherein the effectively superimposing means comprises means for providing an overlaid visual display of the shapes of the successive reflected pulses.

7. Apparatus as in claim 6, wherein the display means comprises means for providing a graph of amplitude as a function of depth in a portion of the region, so that the randomlike variations cause apparent motion in the graph that is discriminably different for normal and abnormal portions of the region; the apparent motion for a normal portion of the region being substantial and erratic in both the amplitude direction and the depth direction; and the apparent motion for an abnormal portion being substantial but cyclic in the amplitude direction, providing the maximum obtainable amplitude, and insubstantial in the depth direction.

8. Apparatus as in claim 3, wherein the effectively superimposing means comprises means for combining the converted successive reflected pulses electrically.

9. Apparatus as in claim 8, wherein the effectively superimposing means comprises also means responsive to the electrically combined pulses for indicating the location of an abnormal portion of the region.

10. Apparatus as in claim 8, wherein the combining means comprises means responsive to the randomlike variations to cause substantial and erratic variations in both the amplitude and the time of the peaks of the combined pulses for a normal portion of the region, and to cause substantial but cyclic variations in the amplitude, providing the maximum obtainable amplitude, and only insubstantial variations in the time of the peaks of the combined pulses for an abnormal region.

11. Apparatus as in claim 10, wherein the effectively superimposing means comprises also means responsive to the amplitude and the time of the peaks of the combined pulses for indicating the location of an abnormal portion of the region.

* * * * *